United States Patent
Seremjian

(10) Patent No.: US 8,905,297 B2
(45) Date of Patent: *Dec. 9, 2014

(54) METHOD AND APPARATUS FOR IDENTIFYING AND TRACKING BIOLOGICAL FLUID

(71) Applicant: Kip Seremjian, Kenosha, WI (US)

(72) Inventor: Kip Seremjian, Kenosha, WI (US)

(\*) Notice: Subject to any disclaimer, the term of this patent is extended or adjusted under 35 U.S.C. 154(b) by 0 days.

This patent is subject to a terminal disclaimer.

(21) Appl. No.: 14/066,684

(22) Filed: Oct. 29, 2013

(65) Prior Publication Data

US 2014/0054366 A1  Feb. 27, 2014

Related U.S. Application Data

(63) Continuation of application No. 12/738,368, filed as application No. PCT/US2008/080509 on Oct. 20, 2008, now Pat. No. 8,567,663.

(60) Provisional application No. 60/981,413, filed on Oct. 19, 2007.

(51) Int. Cl.

| | |
|---|---|
| *G06F 17/00* | (2006.01) |
| *G06F 19/00* | (2011.01) |
| *A61J 1/14* | (2006.01) |
| *G06Q 50/22* | (2012.01) |
| *A61J 1/10* | (2006.01) |
| *A61B 19/00* | (2006.01) |
| *A61J 1/16* | (2006.01) |

(52) U.S. Cl.
CPC .............. *G06Q 50/22* (2013.01); *A61J 2200/72* (2013.01); *A61J 1/10* (2013.01); *G06F 19/366* (2013.01); *A61B 2019/448* (2013.01); *A61J 2205/10* (2013.01); *A61J 2205/30* (2013.01); *A61J 2205/20* (2013.01); *A61J 1/1462* (2013.01); *A61B 19/44* (2013.01); *A61J 1/16* (2013.01); *A61J 2205/60* (2013.01)
USPC .......................................... 235/375

(58) Field of Classification Search
CPC ............ G01N 1/00; A61B 1/00; A61B 19/44; A61B 2019/448; A61J 1/05; A61J 1/10; A61J 1/16; A61J 2200/70; A61J 2205/00; A61J 2205/60; G06F 19/366
USPC .............................. 235/375, 451, 492; 705/2, 3
See application file for complete search history.

(56) References Cited

U.S. PATENT DOCUMENTS

| | | | | |
|---|---|---|---|---|
| 5,401,110 | A * | 3/1995 | Neeley | 400/621 |
| 6,285,285 | B1 * | 9/2001 | Mongrenier | 340/572.8 |
| 6,659,338 | B1 * | 12/2003 | Dittmann et al. | 235/375 |
| 2004/0129769 | A1 * | 7/2004 | Kovach | 235/375 |
| 2006/0054694 | A1 * | 3/2006 | Auchinleck | 235/385 |

\* cited by examiner

*Primary Examiner* — Tuyen K Vo
(74) *Attorney, Agent, or Firm* — Richards Patent Law P.C.

(57) ABSTRACT

A system and method of tracking biological fluid during a donation process. The system and method identify and release blood products from quarantined storage and print an appropriate blood bag label on demand.

17 Claims, 6 Drawing Sheets

METHOD AND APPARATUS FOR IDENTIFYING AND TRACKING BIOLOGICAL FLUID

RELATED APPLICATIONS

This application is a non-provisional of and claims priority to U.S. Provisional Patent Application Ser. No. 60/981,413 filed on Oct. 19, 2007, the entire contents of which are incorporated herein by reference.

BACKGROUND OF THE INVENTION

The current blood collection process is a manual check and balance system that uses extensive manual labor and relies on human multi-layer verification. The process consists of manual data entry of lab results and double, triple, and quadruple checks of numerous steps of the donation, manufacturing and quarantine release processes. The present process is prone to errors.

The current blood collection process can be described as follows:
1. Donor center blood collection "kits" consist of blood bags and sample vials labeled with a unique bar code label requiring two individuals to check and verify correct label identification.
2. A blood sample is collected from the donor just prior to collecting a pint of blood in the blood bag.
3. Blood bags containing collected blood are placed in quarantine pending lab results.
4. Blood samples are sent to laboratory for analysis.
5. Lab results for specific units of blood are faxed or emailed to donor center blood bank.
6. Each test result is recorded two separate times by two different individuals as a check and balance. Verification of received lab results is reviewed by two individuals at management level.
7. Worker gang-prints approved and rejected labels using lab results.
8. Quarantined blood is removed from refrigerated quarantine storage for acceptance or destruction release labeling by four individuals.
9. Worker1 places blood on counter while reading the unique bag number to worker2 who checks the bag number against the lab results list while worker3 verifies the bag number against the lab results number and applies the label to the bag and reads off bag number. Worker4 verifies.
10. Approved bags are collected, placed on trays and verified again by workers in step #9 before placing approved bags in approved storage location. Process is repeated for rejected blood bags.

SUMMARY OF THE INVENTION

The invention provides a system and method of 1) accurately, safely and effectively identifying and releasing blood products from quarantined storage; 2) directly printing the appropriate blood bag label on demand; 3) reducing errors for matching data to blood product; and 4) improving labor efficiency.

The system monitors and maintains blood status as quarantined while a software program "listens" for laboratory data. Upon receipt of the blood lab results from either the blood tracking system or other compatible blood bank labeling systems (e.g., Ilematrax), the software program: (1) processes and parses the lab data creating records for each blood bag, (2) verifies the results with the corresponding bag, (3) checks for human and hardware errors, (4) verifies the laboratory donor ID against the blood bag donor ID, and (5) writes the proper print sequence code to produce a required ISTB-128 compatible label to the chip on the corresponding blood bag. The software program confirms data integrity and changes the blood status to approved or rejected (depending on the lab results), updates the blood status change to the smart cradle and the corresponding blood bag and switches the smart cradle and the smart tray lights from yellow to green or red, respectively.

When blood is released and ready for labeling, the blood bag is removed from quarantine and the memory chip on the bag is touched to the printer interface box. The appropriate label is printed based on data in the memory chip for application to the blood bag.

The invention can incorporate emerging technologies such as nanodetectors, miniaturized sensors/detectors, "lab on a chip" analytical testing platforms or other future devices that can be interfaced with the processor.

One embodiment of the present invention provides a biological fluid identification and tracking system. The system comprises a computer processor in communication with a network, a tray in communication with the network and positioned within a refrigerated compartment, the tray including a controller and a plurality of bins configured to support a container and a display associated with each bin, each of the displays configured to indicate whether testing of the container within the associated bin is complete, a module having an interface configured for direct contact with a memory chip on the container, the module configured to read information stored on the memory chip, and a printer coupled to the module and configured to print a label including at least a portion of the information stored on the memory chip.

Another embodiment of the present invention provides a method of tracking biological fluid. The method comprises collecting biological fluid from a donor and storing the biological fluid in a container, writing a donor identification to a memory chip secured to the container and associating the donor identification to a unique memory chip identification, positioning the container in a tray located in a quarantine location, connecting the memory chip to a controller associated with the tray, the controller in communication with a network, transmitting a signal to the controller when a testing process of the biological fluid is complete, displaying an indication related to the signal, connecting the memory chip to an interface to read data on the memory chip, and printing a label for the container including at least a portion of the read data.

In yet another embodiment, the present invention provides a biological fluid identification and tracking system comprising a tray assembly, a server, and a printer. The tray assembly includes a controller in communication with a network, a plurality of bins, each bin configured to receive a container of biological fluid, a plurality of ports in communication with the controller, each port associated with a bin, plurality of displays, each display in communication with an associated port, and a cradle configured to connect to the port and to a memory chip on the container. The server is in communication with the controller and a network and is configured to receive via the network laboratory test data associated with the container, and transmit a signal via the port to the memory chip and the display associated with the container, the signal including data related to the laboratory test data. The printer is configured to print a label for the container, the label including information related to the laboratory test data.

Other aspects of the invention will become apparent by consideration of the detailed description and accompanying drawings.

DETAILED DESCRIPTION

Figure 1:
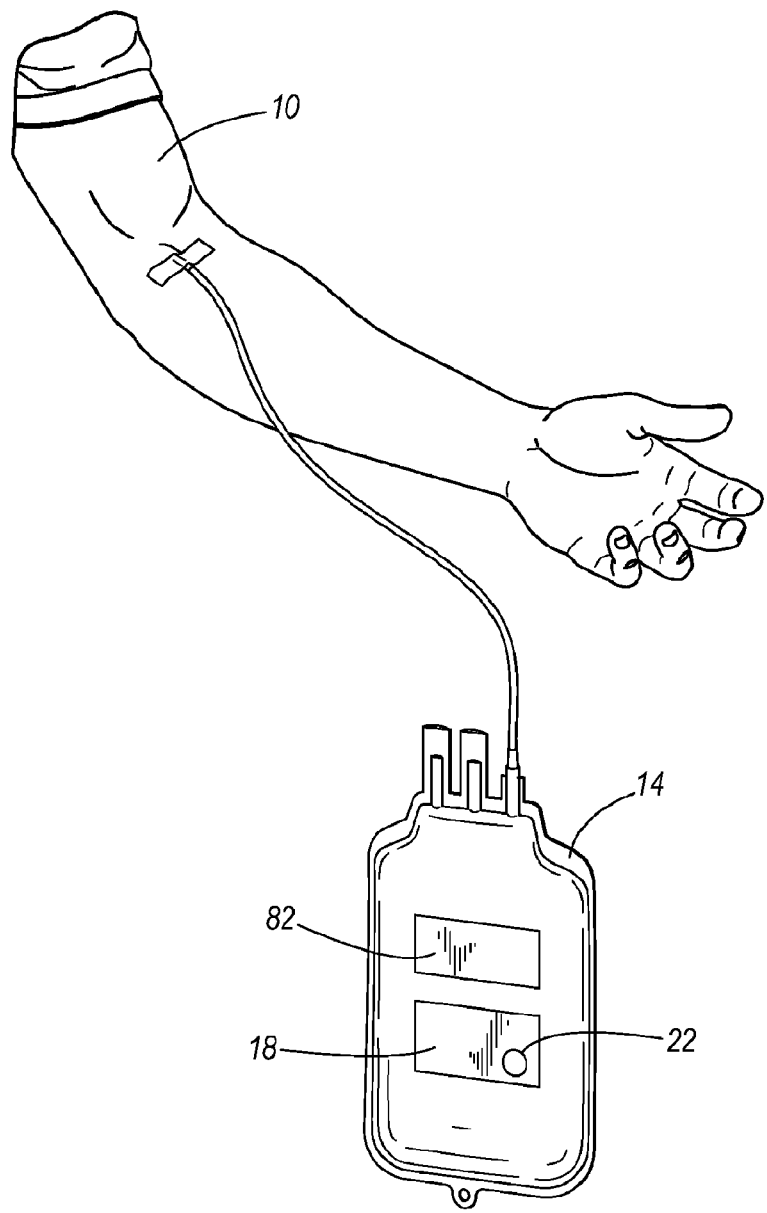
FIG. 1 is a perspective view of blood being collected from a donor.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Prior to blood donation, unique identifying barcode labels are applied to a blood bag and sample vials, and a memory chip with a unique identification number is secured to the blood bag. At the time of blood collection, the bar-coded blood bag with its memory chip and bar-coded blood sample vials are scanned and programmed into the blood bag's memory chip (e.g., a unique ROM ID chip using a barcode reader equipped with a 9092 type chip socket). The donor identification also is programmed into the memory chip.

FIG. 1 illustrates a process of collecting biological fluid, such as blood, from a donor 10. Blood can be separated into its components such as red blood cells, white blood cells, plasma, platelets, and cryoprecipitate. In a typical process, the donor 10 is phlebotomized and the blood is collected in a sterile container 14. The container 14 generally includes preservatives and anti-clotting compounds. The container 14 includes a label 18, such as a barcode label and a memory chip 22. The memory chip 22 is secured to the container 14. The chip 22 can store donor identification information, the container barcode number and unique chip ROM TD. The blood can be separated and each component placed in its own individual container 14.

An example of a memory chip 22 that can be used with the present invention is a microcan, such as the Touch Memory F5 model available from Dallas Semiconductors. The memory chip 22 can be attached to an exterior surface of the container 14 with adhesive or other suitable means. The memory chip 22 also can include a processor and one or more sensors operable to sense environmental factors, such as temperature, time, and date.

Figure 2:
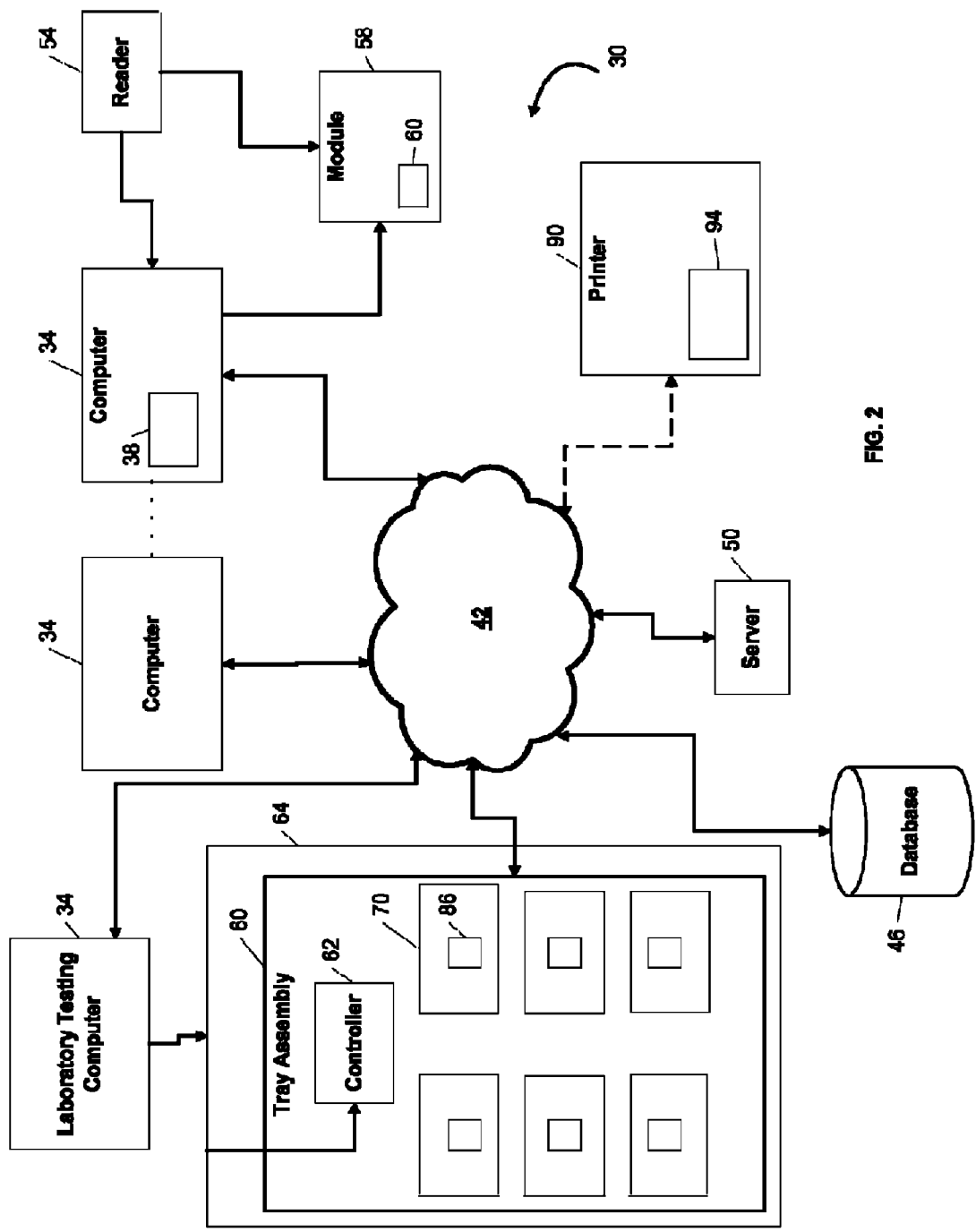
FIG. 2 is a schematic illustration of a biological fluid identification and tracking system according to one embodiment of the present invention.

After the blood is collected from the donor 10, the container 14 is quarantined in a refrigerated storage area for a period of time. The container 14 remains in quarantine awaiting laboratory results. While the container 14 is in quarantine, the container 14 is in communication with a biological fluid identification and tracking system 30 according to one embodiment of the present invention. The biological fluid identification and tracking system 30 is schematically illustrated in FIG. 2 and utilizes a unique electronic methodology for the positive release of quarantined blood and generation of on-demand, accurate ISTB-128 compatible labels. The system 30 ensures the safe verification of blood data with blood product and reduces the labor required to process blood lab data with blood product. The system 30 also streamlines the process by automating the release of quarantined blood and eliminates the labor required and potential for error in blood bag labeling. The system 30 uses hardware and software to electronically identify, scan, and verify blood bags, store blood data records, and print labels. The system 30 also tracks containers 14 for purposes of inventory control.

The system 30 includes a computer 34, which includes an operating system for running various software programs and/or a communications application. In particular, the computer 34 can include a software program(s) 38 that operates to communicate with the memory chip 22. The software program(s) 38 is operable to receive data from external software programs and hardware and it is noted that data may be input to the software program(s) 38.

The computer 34 can include any suitable input/output device adapted to be accessed by personnel. The computer 34 can include typical hardware such as a processor, I/O interfaces, and storage devices or memory. The computer 34 can also include input devices such as a keyboard and a mouse. The computer 34 can further include standard output devices, such as a monitor. In addition, the computer 34 can include peripherals, such as a printer and a scanner.

The computer 34 can be networked with other computers 34 via network 42. The other computers 34 may include additional and/or different computer programs and software and are not required to be identical to the computer 34, described above. The computers 34 can also communicate with a database(s) 46 and a server(s) 50. It is noted that the software program(s) 38 could also reside on the server(s) 50.

The network 42 can be built according to any suitable networking technology or topology or combinations of technologies and topologies and can include multiple sub-networks. Connections between the computers shown in FIG. 2 can be made through local area networks ("LANs"), wide area networks ("WANs"), public switched telephone networks ("PSTNs"), wireless networks, Intranets, the Internet, or any other suitable networks.

The two-way arrows in FIG. 2 generally represent two-way communication and information transfer between the network 42 and any one of the computers 34 shown in FIG. 2. However, for some computerized equipment, only one-way communication and information transfer may be necessary.

The system 30 includes a data reader 54 operable to read information on the label 18 and transmit or input the information to the computer 34. The reader 54 also may transmit or input the information directly into the database 46. In one construction, the reader 54 is operable to read bar codes on the label 18.

The system 30 also includes a module 58 adapted to communicate with the memory chip 22. The module 58 can be standalone or coupled to the computer 34 and/or reader 54. The module 58 is adapted to input or write the information on the label 18 that is read by the reader 54 to the memory chip 22. Additional data or information may be input or written to the memory chip 22, such as a patient identifier or a name or an identifier of a person collecting the biological fluid from the donor 10. The module 58 can include an interface 60 that is adapted to directly contact the memory chip 22 and electronically communicate the information to the memory chip 22 and/or read information stored on the memory chip 22.

Figure 3:
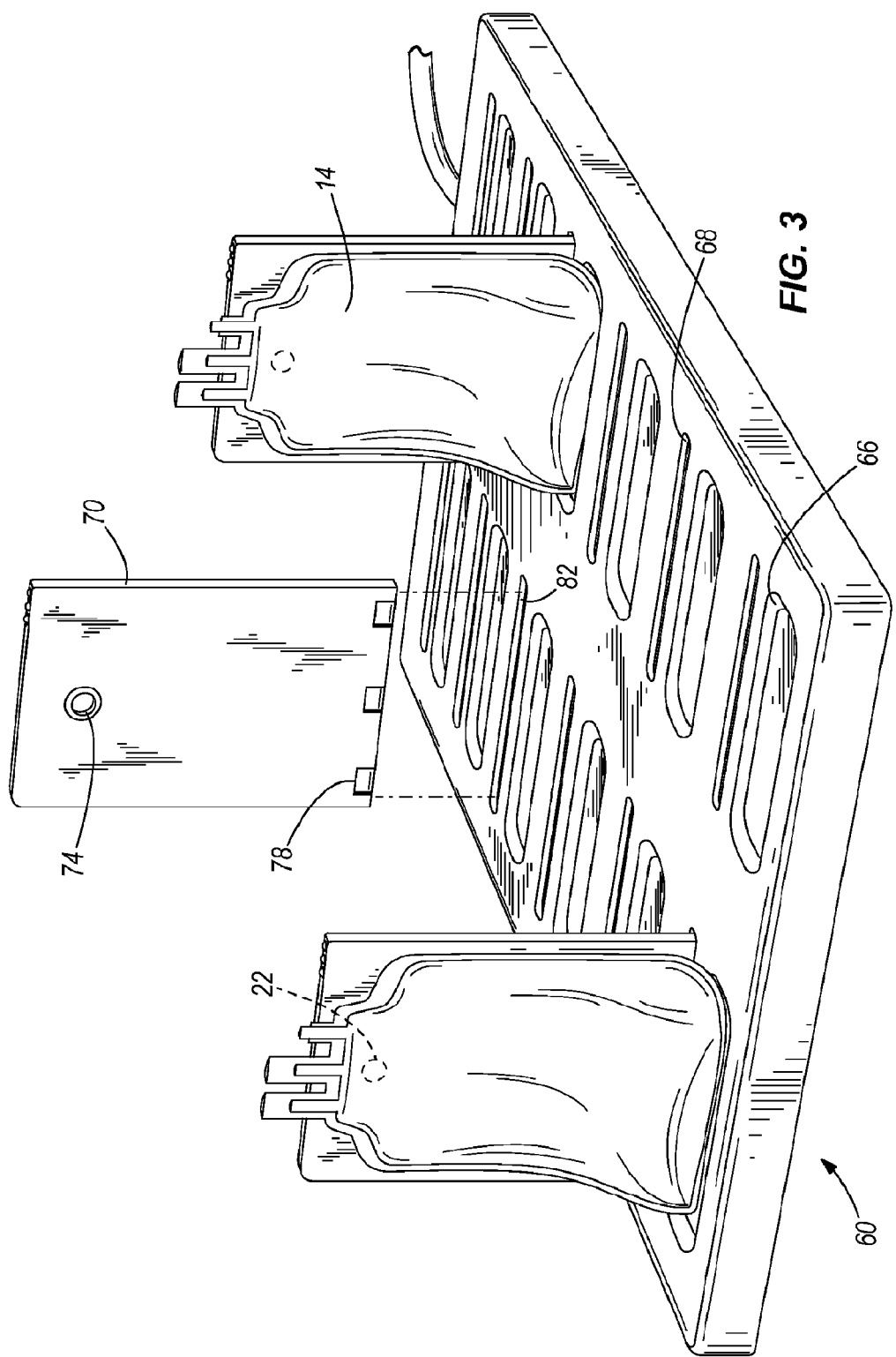
FIG. 3 is a perspective view of a tray assembly used with the system illustrated in FIG. 2 according to one embodiment of the present invention.
Figure 4:
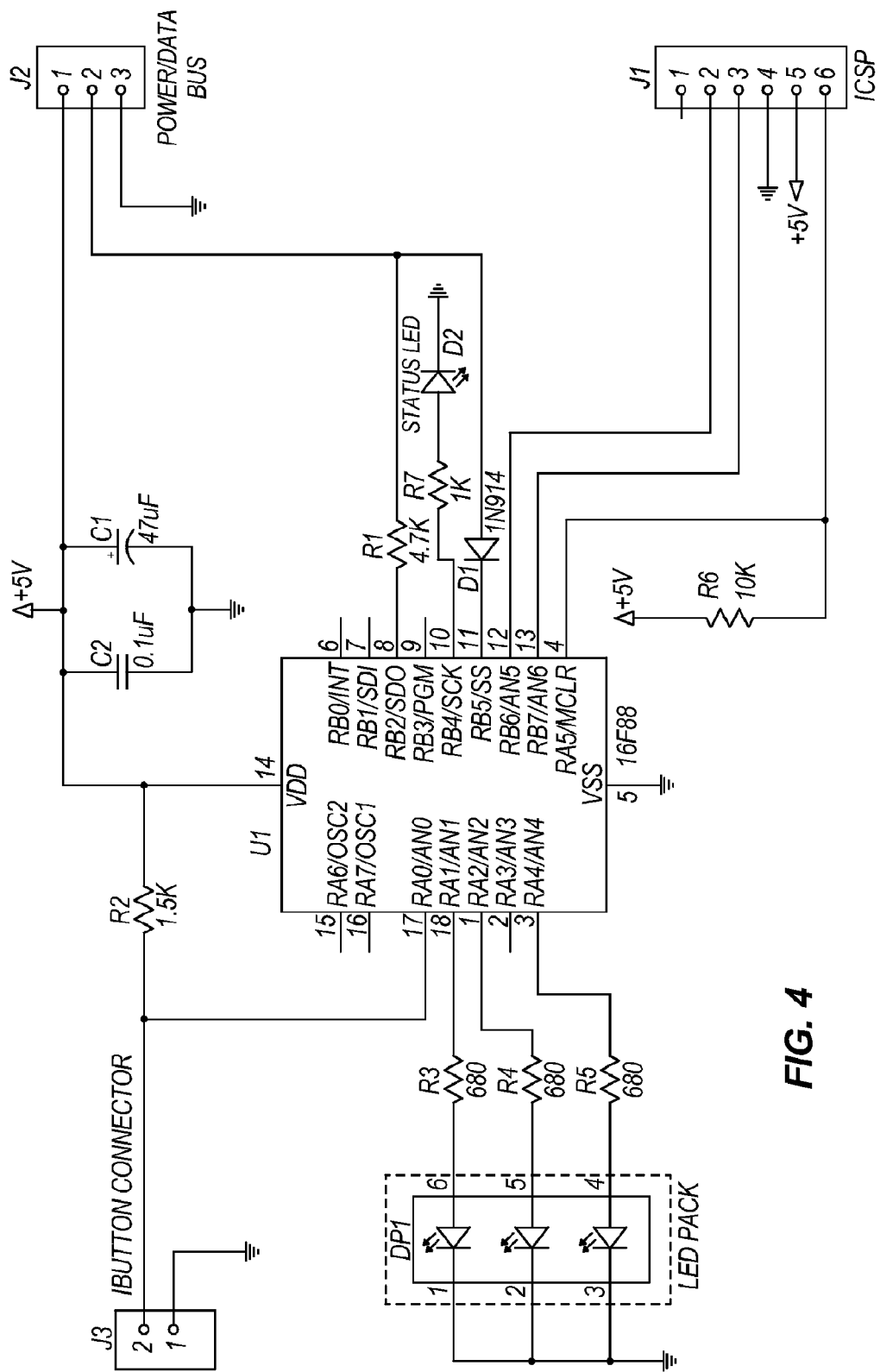
FIG. 4 is a schematic of the tray assembly illustrated in FIG. 3.

The system 30 also includes a tray assembly 60 where the container 14 is stored until laboratory testing results indicate that the biological fluid is safe for distribution and use. The tray assembly 60, illustrated in FIG. 3, for example, is positioned within a refrigerated compartment 64 and can include a controller 62 in communication with the refrigerated compartment 64, the computer 34, and/or the network 42. The controller 62 can communicate with a standalone computer, similar to the computer 34 described above, or with a computer (e.g., laboratory testing computer, database, and/or server) or other processor via the network 42. A plurality of tray assemblies 60 can be positioned within the refrigerated compartment 64 and be connected (e.g., via USB connector) to a main panel in the refrigerated compartment 64, which is in communication with the network 42.

The tray assembly 60 includes a tray having planar surface with one or more apertures or bins 66 formed therein and configured to receive a container 14. Each bin 66 includes an adjacent associated slot 68 configured to receive a cradle 70 coupled to a container 14 to assist the container 14 to remain stored generally in an upright position. The cradle 70 includes a first connector 74 configured to receive and/or be at least in communication with the memory chip 22 of a container 14 and a second connector 78 configured to engage a port 82 supported by the tray assembly 60. The port 82 is in communication with the first connector 74, the controller 62, and the network 42 and/or computer 34. The cradle 70 may include a processor. It is noted that the configuration of each bin 66 may deviate from the shape illustrated in FIG. 3 and that each bin 66 can take on its own configuration and/or shape. Each bin 66 also may include a wall at least partially surrounding the bin 66 to assist the container 14 to remain in a generally upright position. Each bin 66 can hold one or more containers 14.

Each bin 66 includes a display 86 in communication with the port 82 and/or the network 42 and operable to indicate whether the bin 66 includes one or more containers 14 that have completed test results. The display 86 can be coupled to the bin 66 or the plurality of displays 86 can be coupled to a common control panel located inside of, outside of, or near the tray assembly 60. Alternatively, the display 86 can be coupled to the cradle 70. The display 86 can communicate with the computer 34 or standalone computer (or other computer via the network 42) via the port 82 to receive instructions and display data indicative of the test results of the biological fluid. In one construction, the display 86 can include a plurality of light emitting diodes where certain colors indicate the status of one or more containers 14 within the particular bin 66. For example, one light emitting diode can be green that, when illuminated, may indicate that one or more containers 14 have completed and acceptable test results and is ready for further processing. One light emitting diode can be yellow that, when illuminated, may indicate that one or more of the containers 14 in the particular bin 66 are still in the testing process or phase. One light emitting diode can be red that, when illuminated, may indicate that one or more of the containers 14 in the particular bin 66 have completed test results and need to be removed from the cradle 60 and disposed of or processed for further testing. Of course, it will be appreciated that other colors for the light emitting diodes can be utilized and that other suitable displays or indicators may also be used with the present invention.

The server 50 and/or computer 34 periodically check or scan each tray assembly 60 to determine if any of the containers 14 stored therein are ready for further processing or whether any of the containers 14 require disposal or further testing. The server 50 receives lab test data from the laboratory computer 34, parses, and stores the lab results into a results table based on the donor identification. The server 50 also can update local (ARC, AABB) or national (DoD DBITs) databases with the test results. If the lab results do not have a matching donor identification number on any of the containers 14 stored in the refrigerated compartment 64, the server 50 can update the database 46 and/or an error file. The error file can indicate if there is no associated data on a memory chip 22 for the particular donor identification, that the container 14 has already been processed, that an incorrect container 14 was previously removed from the refrigerated compartment 64, that the lab results are for a different donor, or that there is a problem with the hardware.

If the lab results identification, the donor identification, and the unique memory chip identification received from the laboratory computer 34 match, the server 50 transmits the corresponding lab data to the controller 62 to write certain information (e.g., lab test results) onto the memory chip 22 of the associated container 14. The lab results (and any associated information) also can be maintained in the database 46. It is not required that the lab results be written to and stored on the memory chip 22. The server 50 also transmits an instruction to the associated display 86 to indicate that the test results for that particular container 14 have been completed. The display 86 also can indicate whether the container 14 is approved for further processing or is rejected. The server 50 also transmits data to the associated memory chip 22 to store certain information related to the data to be printed on a label for the container 14.

Figure 5:
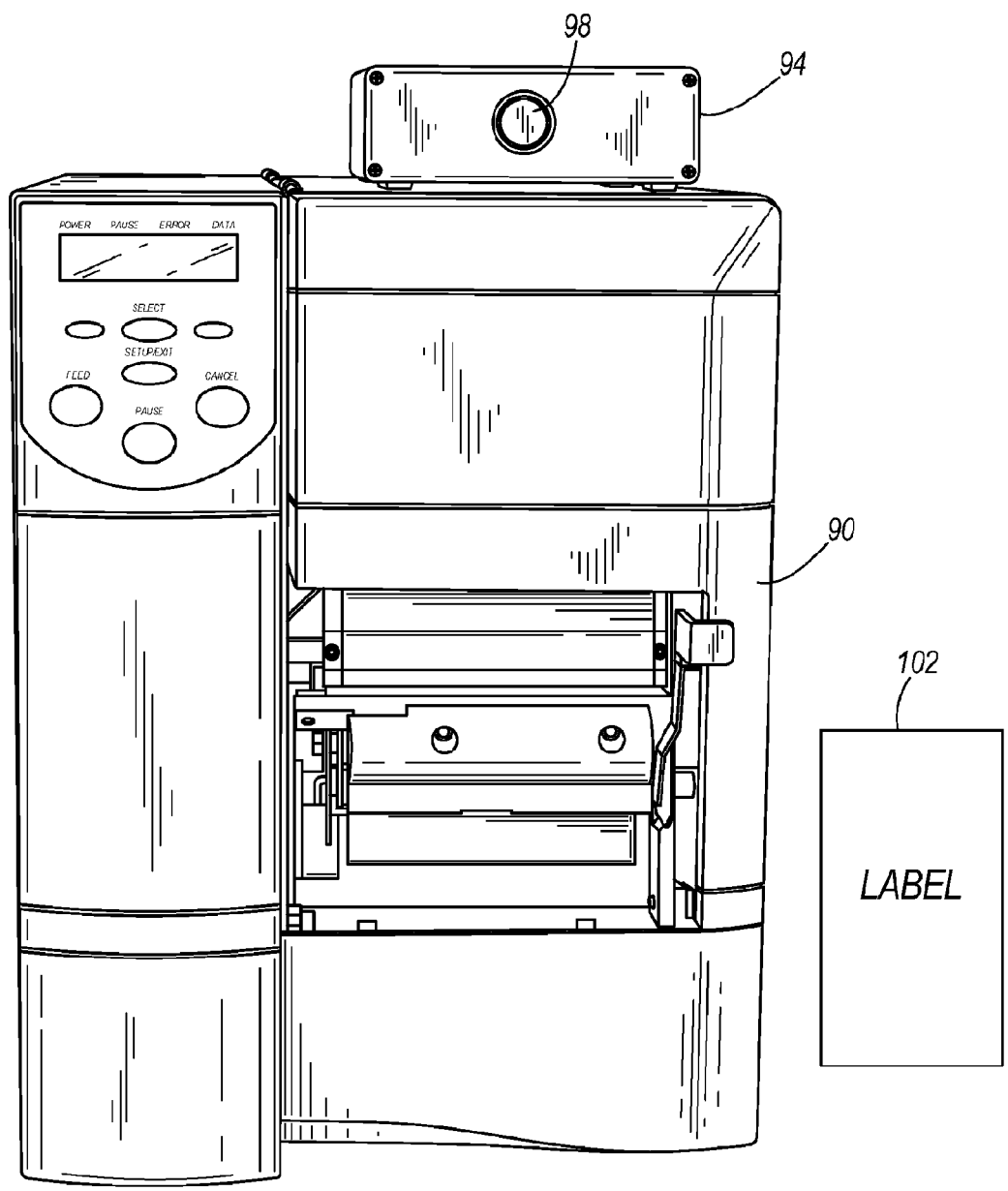
FIG. 5 is a perspective view of a printer used with the system illustrated in FIG. 2 according to one embodiment of the present invention.

The containers 14 that have acceptable test results and are ready for further processing are removed and generally transported to a standalone or networked printer 90 (see FIG. 5, for example) to be labeled. The printer 90 can include a module 94, similar to module 58 described above, that is operable to communicate with the memory chip 22. The module 94 can include a processor and an interface 98 that is configured to directly contact the memory chip 22 and electronically read the information from the memory chip 22. The information stored in the memory chip 22 can be read by the module 94 when the memory chip 22 makes contact with the module 94. The information from the label 18 and additional information added to the memory chip 22 throughout the process that was stored on the memory chip 22 can be accessed by the module 94 to retrieve the test results stored in the printer 90 and/or retrievable from the network 42 and/or computer 34 for the particular container 14. The printer 90 can print one or more secondary labels 102 with additional information such as the test results. The module 94 also can transmit or write the additional information to the memory chip 22. This process ensures that the correct label 102 is placed on the correct container 14. In addition, the memory chip 22 records the number of times a label 102 has been printed for a particular container 14 and prints this information on the label 102 for label inventory purposes.

Figure 6:
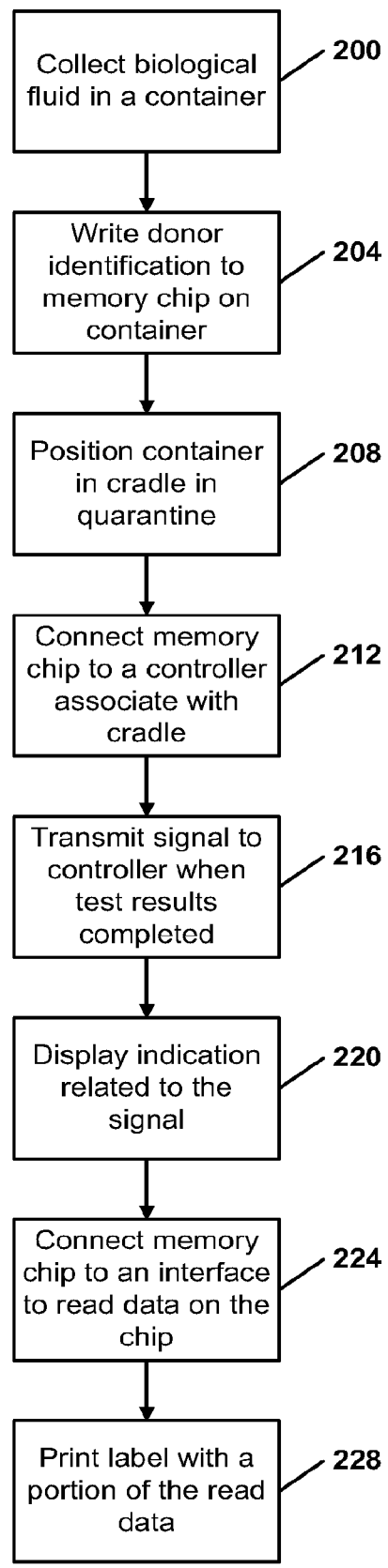
FIG. 6 is a flow chart of a method of tracking biological fluid according to one embodiment of a method of the invention.

FIG. 6 is a flow chart illustrating a method of tracking biological fluid according to one embodiment of a method of the invention. A nurse or other appropriate personnel collects (at 200) a biological fluid such as blood from a donor that is stored in a container 14. The container 14 includes a memory chip 22 having a unique identification. The personnel scans a donor identification which is written (at 204) to the memory chip 22. The donor identification is associated with the unique memory chip identification. After the scanning process, the container 14 is positioned (at 208) on the tray assembly 60 within a refrigerated compartment 64 also indicated as a quarantine location. The user connects (at 212) the memory chip 22 on the container 14 to the connector 74 on the cradle 70 and the cradle 70 to the port 82 such that the memory chip 22 is in communication with the controller 62, which is associated with the tray assembly 60. When the server 50 receives the lab test results, the server transmits (at 216) a signal to the controller 62. The controller 62 transmits the signal to the appropriate display 86 to display (at 220) an indication related to the signal such as an accept or reject indication. Upon completion of the laboratory test results, the user can remove the container 14, take the container 14 to the printer 90, and connect (at 224) the memory chip to the interface 98 to read the data on the memory chip 22. The printer 90 prints (at 228) a label for the container 14 including at least a portion of the read data (e.g., donor identification, laboratory test results, and the like).

Various features and advantages of the invention are set forth in the following claims.

What is claimed is:

1. A biological fluid identification and tracking system comprising:
    a computer processor in communication with a network;
    a tray assembly in communication with the network and positioned within a refrigerated compartment, the tray assembly including a controller and a plurality of bins configured to support a container and a display associated with each bin, each of the displays configured to indicate whether testing of the container within the associated bin is complete; and
    a module having an interface configured for direct contact with a memory chip on the container, the module configured to read information stored on the memory chip.

2. The biological fluid identification and tracking system of claim 1 further comprising a port associated with each bin, the port in communication with the controller.

3. The biological fluid identification and tracking system of claim 2 further comprising a cradle having a first connector connected to the memory chip of an associated container and a second connector configured to engage the port of the associated bin.

4. The biological fluid identification and tracking system of claim 1 further comprising a server in communication with the controller, the server configured to transmit a signal to the controller having an instruction related to whether testing of the container is complete.

5. The biological fluid identification and tracking system of claim 1 wherein the controller transmits the signal to the display to indicate a disposition of the container associated with the display.

6. The biological fluid identification and tracking system of claim 1 wherein the memory chip includes at a minimum, a donor identification and a memory chip identification prior to placement on the tray assembly.

7. The biological fluid identification and tracking system of claim 6 wherein a server in communication with the controller is configured to transmit a signal to the controller having an instruction related to whether testing of the container is complete only after verifying that the donor identification, the memory chip identification, and a laboratory results identification match.

8. A method of tracking biological fluid, the method comprising:
    collecting biological fluid from a donor and storing the biological fluid in a container;
    writing a donor identification to a memory chip secured to the container and associating the donor identification to a unique memory chip identification;
    positioning the container in a tray assembly located in a quarantine location;
    connecting the memory chip to a controller associated with the tray assembly, the controller in communication with a network;
    transmitting a signal to the controller when a testing process of the biological fluid is complete;
    displaying an indication related to the signal; and
    connecting the memory chip to an interface to read data on the memory chip.

9. The method of tracking biological fluid of claim 8 further comprising storing a number of times the label is printed onto the memory chip.

10. The method of tracking biological fluid of claim 8 further comprising verifying the donor identification, the unique memory chip identification, and a laboratory results identification match prior to transmitting the signal to the controller when a testing process of the biological fluid is complete.

11. The method of tracking biological fluid of claim 8 further comprising verifying the donor identification, the unique memory chip identification, and a laboratory results identification match prior to transmitting the signal to the controller when a testing process of the biological fluid is complete.

12. The method of tracking biological fluid of claim 8 further comprising writing at least a portion of data associated with the testing process to the memory chip.

13. The method of tracking biological fluid of claim 8 further comprising transmitting results of the testing process to a national biological fluid database.

14. The method of tracking biological fluid of claim 8 wherein the quarantine location is refrigerated.

15. A biological fluid identification and tracking system comprising:
   a tray assembly including
      a controller in communication with a network,
      a plurality of bins, each bin configured to receive a container of biological fluid,
      a plurality of ports in communication with the controller, each port associated with a bin,
      a plurality of displays, each display in communication with an associated port, and
      a cradle configured to connect to the port and to a memory chip on the container; and
   a server in communication with the controller and a network, the server configured to receive via the network laboratory test data associated with the container, and transmit a signal via the port to the memory chip and the display associated with the container, the signal including data related to the laboratory test data.

16. The biological fluid identification and tracking system of claim 15 further comprising a module including an interface configured to directly contact the memory chip on the container to retrieve data stored on the memory chip.

17. The biological fluid identification and tracking system of claim 15 wherein the display upon receiving the signal is configured to display an indication related to the laboratory test data.

* * * * *